United States Patent
Yoshimura et al.

(10) Patent No.: US 7,642,374 B2
(45) Date of Patent: Jan. 5, 2010

(54) PROCESS FOR PRODUCING 5-IODO-2-METHYLBENZOIC ACID

(75) Inventors: Takafumi Yoshimura, Niigata (JP); Toshio Hidaka, Ibaraki (JP); Yoshifumi Sato, Niigata (JP); Norio Fushimi, Okayama (JP); Kazuhiro Yamada, Aichi (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 4 days.

(21) Appl. No.: 10/563,088

(22) PCT Filed: Jul. 1, 2004

(86) PCT No.: PCT/JP2004/009696

§ 371 (c)(1),
(2), (4) Date: Dec. 30, 2005

(87) PCT Pub. No.: WO2005/003073

PCT Pub. Date: Jan. 13, 2005

(65) Prior Publication Data

US 2006/0167312 A1 Jul. 27, 2006

(30) Foreign Application Priority Data

Jul. 3, 2003 (JP) ............................. 2003-270652
Nov. 4, 2003 (JP) ............................. 2003-374481
Nov. 4, 2003 (JP) ............................. 2003-374482
Nov. 4, 2003 (JP) ............................. 2003-374483

(51) Int. Cl.
C07C 51/42 (2006.01)

(52) U.S. Cl. ...................................... 562/494; 570/182

(58) Field of Classification Search ................. 570/203, 570/182, 205, 211, 243, 246, 247, 261; 562/493, 562/494; 560/103
See application file for complete search history.

(56) References Cited

U.S. PATENT DOCUMENTS 4,778,940 A 10/1988 Rule et al.
4,788,353 A 11/1988 Paparatto et al.
4,788,354 A 11/1988 Paparatto et al.
5,892,138 A * 4/1999 Singh et al. ................. 570/208

FOREIGN PATENT DOCUMENTS

| EP | 0154236 | 9/1985 |
| EP | 1595862 | 11/2005 |
| JP | 59-219241 | 12/1984 |
| JP | 2003-012597 | 1/2003 |
| JP | 2003012597 A * | 1/2003 |
| JP | 2003089673 A * | 3/2003 |

OTHER PUBLICATIONS

English Translation of JP2003012597, Igari et al.*
English Translation of JP200389673, Aizawa et al.*
Supplementary European Search Report for Application No. EP 04 74 7165, dated Jun. 20, 2007.

* cited by examiner

*Primary Examiner*—Jafar Parsa
*Assistant Examiner*—Sudhakar Katakam
(74) *Attorney, Agent, or Firm*—Antonelli, Terry, Stout & Kraus, LLP.

(57) ABSTRACT

The present invention provides a process for producing 5-iodo-2-methylbenzoic acid through iodination of 2-methylbenzoic acid, the process including, as essential steps, a reaction step of iodinating 2-methylbenzoic acid in the presence of a microporous compound, iodine, an oxidizing agent, and acetic anhydride, and a purification step including sublimation, distillation, crystallization, or a combination of two or more of these. According to the present invention, 5-iodo-2-methylbenzoic acid, which is useful for producing functional chemicals such as drugs, can be produced at high purity and high yield in a simple manner. Since the production process includes a simple reaction step and a simple separation/purification step, the load of purification is mitigated. In addition, the microporous compound such as a zeolite catalyst which has been separated and recovered from the reaction mixture can be repeatedly employed after performing of a simple treatment. Thus, the production process ensures a long service life of catalysts and high efficiency.

15 Claims, No Drawings

PROCESS FOR PRODUCING 5-IODO-2-METHYLBENZOIC ACID

TECHNICAL FIELD

The present invention relates to a process for producing 5-iodo-2-methylbenzoic acid, which serves as a useful source for drugs, agricultural chemicals, and functional chemicals, and to high-purity 5-iodo-2-methylbenzoic acid. More particularly, the invention relates to an effective process for producing 5-iodo-2-methylbenzoic acid at high yield and high selectivity through iodination of 2-methylbenzoic acid, and to high-purity 5-iodo-2-methylbenzoic acid produced through the process.

BACKGROUND ART

There have been known methods for synthesizing 5-iodo-2-methylbenzoic acid, such as a method in which 2-methylbenzoic acid is reacted with iodine in the co-presence of sodium nitrite and fuming sulfuric acid (Journal of the Indian Chemical Society (1930), p. 503 to 504) and a method in which 2-methylbenzoic acid is reacted with potassium iodide in the co-presence of thallium(III) trifluoroacetate (Journal of the Chemical Society. Perkin Transactions I. (1974), p. 2405 to 2409). The former method attains a yield as remarkably low as 18% and employs a large amount of a mixture of sodium nitrite and fuming sulfuric acid, serving as strong oxidizing agents (reaction reagent), requiring safe handling of the mixture. The latter method attains a yield as low as 33% and employs a highly toxic thallium salt, making the method inappropriate for producing 5-iodo-2-methylbenzoic acid on an industrial scale.

Other possible approaches are iodination techniques generally employed for aromatic compounds, such as the Sandmayer process in which an aromatic amine is subjected to diazo removal and iodination (Organic Syntheses, Collective Vol. II (1943), p. 351); the transhalogenation method in which chlorination or bromination is performed, followed by substitution of Cl or Br by I (Organic Syntheses, Collective Vol. V (1973), p. 478); a method employing iodine monochloride (Russian Journal of Organic Chemistry, 34, 7 (1998), p. 997 to 999); and methods in which iodine and sodium periodate are employed in the presence of an acid catalyst (Bulletin of the Chemical Society of Japan, vol. 73 (2000), p. 951 to 956, and Japanese Patent Application Laid-Open (kokai) No. 2003-12597).

In the case in which 5-iodo-2-methylbenzoic acid is synthesized through the aforementioned Sandmayer process, a multi-step reaction including nitration, reduction, diazotization, and diazo removal-iodination must be performed. Steps such as nitration and diazotization are problematic in safety, making the overall process very cumbersome. The transhalogenation method requires two reaction steps and a purification step, making the overall process cumbersome. In addition, since sodium iodide, potassium iodide, or a similar iodine compound is used in a large, excessive amount for introduction of iodine, such an excessive compound must be separated and collected after completion of reaction through burdensome steps, thereby increasing production cost.

Meanwhile, the above method employing iodine monochloride is a simple method which can be carried out through a single-reaction step. However, when iodine monochloride is reacted with an aromatic compound having an electron-attractive group such as a benzoic acid compound, high reaction efficiency cannot be attained, due to low reactivity. For example, the document disclosing the aforementioned method employing iodine monochloride describes iodination of benzoic acid, with the yield of 3-iodobenzoic acid as a product being about 43%, which is unsatisfactory. When the method is applied to iodination of 2-methylbenzoic acid, high yield is difficult to attain.

As mentioned above, iodination methods employing iodine and an oxidizing agent such as iodic acid or periodic acid are conventionally known. For example, in the method wherein iodine and sodium periodate are employed in the presence of an acid catalyst (Bulletin of the Chemical Society of Japan, vol. 73 (2000), p. 951 to 956), a comparatively high reaction efficiency can be attained even when an aromatic compound having an electron-attractive group is reacted. However, since the method employs a large amount of sulfuric acid, burdensome treatment of waste sulfuric acid must be performed after reaction. Thus, in practice the iodination methods are not employed on an industrial scale.

The aforementioned Japanese Patent Application Laid-Open (kokai) No. 2003-12597 discloses a similar iodination method. In the method, 2-methylbenzoic acid is reacted with iodine and periodic acid in the presence of an acid catalyst, to thereby produce a mono-iodated methylbenzoic acid compound. However, product yield described in the Examples is about 52 to 65%, which is unsatisfactory. In addition, purity of the product is as low as about 95%. Thus, in order to obtain high-purity product, an additional purification step is required, making the overall process cumbersome. In this method, a considerable amount of the product still remains dissolved in mother liquor after recovery of the product. Since the mother liquor also contains sulfuric acid serving as a catalyst and other high-boiling-point compounds, separation and recovery of the product is difficult. The above document discloses a technique of recycling the mother liquor in the reaction system, but purity of the product decreases to 90%. Thus, the recycling is not considered appropriate. As described hereinabove, the method disclosed in Japanese Patent Application Laid-Open (kokai) No. 2003-12597 includes an improved step, but still has problems in being carried out on an industrial scale, and process cost remains to be improved.

Upon production of 5-iodo-2-methylbenzoic acid, 3-iodo-2-methylbenzoic acid, which is an isomer of iodo-methylbenzoic acid, is produced as a by-product. Since this isomer is difficult to separate from 5-iodo-2-methylbenzoic acid, 5-iodo-2-methylbenzoic acid of high purity is difficult to obtain. Thus, product purity and isolation yield are problematically unsatisfactory. The aforementioned conventional techniques do not suggest reduction in amounts of undesired isomers. There have already been known some techniques for site-specific iodination of an aromatic compound; e.g., methods including reacting iodine monochloride with an aromatic compound in the presence of zeolite (Catalysis Letters, 40 (1996), p. 257) and methods including oxyiodination of an aromatic compound in the presence of zeolite (Japanese Patent Application Laid-Open (kokai) No. 59-219241 and Japanese Kohyo Patent Publication No. 1-502819). However, in employment of any of these methods, selectivity of reaction is not always satisfactorily attained. In addition, there are very few reports about such reaction of compounds each having a plurality of substituents and an electron-attractive group (e.g., 2-methylbenzoic acid). Thus, according to conventional techniques, an effective method for producing 5-iodo-2-methylbenzoic acid which attains high selectivity and high yield on the basis of iodine has never been developed.

Thus, an object of the present invention is to provide a high-efficiency industrial means for producing 5-iodo-2-methylbenzoic acid through iodination of 2-methylbenzoic acid serving as a starting material, which means is a simple production process and is able to provide a high-purity product at high yield.

DISCLOSURE OF THE INVENTION

The present inventors have carried out extensive studies to solve the aforementioned problems and have found that iodination of 2-methylbenzoic acid serving as a starting material can be performed at high selectivity through iodinating 2-methylbenzoic acid in the presence of a microporous compound, iodine, an oxidizing agent, and acetic anhydride, and that high-purity 5-iodo-2-methylbenzoic acid, which has never been produced through a conventional method, can be readily produced at high yield and high efficiency through combination of the above reaction step and a purification step including sublimation, distillation, and/or crystallization. The present invention has been accomplished on the basis of these findings.

Accordingly, the present invention provides a process for producing 5-iodo-2-methylbenzoic acid and high-purity 5-iodo-2-methylbenzoic acid, as described below.

(1) A process for producing 5-iodo-2-methylbenzoic acid through iodination of 2-methylbenzoic acid, characterized in that the process comprises, as essential steps, a reaction step of iodinating 2-methylbenzoic acid in the presence of a microporous compound, iodine, an oxidizing agent, and acetic anhydride, and a purification step including sublimation, distillation, crystallization, or a combination of two or more of these.

(2) A process for producing 5-iodo-2-methylbenzoic acid according to (1), wherein the microporous compound is a β-form zeolite.

(3) A process for producing 5-iodo-2-methylbenzoic acid according to (2), wherein the β-form zeolite has an Si/Al mole ratio of 10 to 250.

(4) A process for producing 5-iodo-2-methylbenzoic acid according to (3), wherein the β-form zeolite contains an element other than Si, Al, and O, which form a skeleton thereof, within or outside the skeleton.

(5) A process for producing 5-iodo-2-methylbenzoic acid according to (4), wherein the element other than Si, Al, and O, which form a skeleton of the β-form zeolite, is at least one member selected from among Na, K, Cs, Ca, Mg, Ti, Sn, Fe, Ni, Zn, Pb, and Ag.

(6) A process for producing 5-iodo-2-methylbenzoic acid according to (1), wherein the oxidizing agent is iodic acid and/or periodic acid.

(7) A process for producing 5-iodo-2-methylbenzoic acid according to (1), wherein the microporous compound is separated and recovered from a reaction mixture resulting from the reaction step, followed by re-employment in the reaction step.

(8) A process for producing 5-iodo-2-methylbenzoic acid according to (7), wherein the separated and recovered microporous compound is calcined, followed by re-employment in the reaction step.

(9) A process for producing 5-iodo-2-methylbenzoic acid according to (8), wherein the separated and recovered microporous compound is washed with a solvent, followed by calcining.

(10) A process for producing 5-iodo-2-methylbenzoic acid according to (9), wherein the separated and recovered microporous compound is washed with acetic acid serving as the solvent.

(11) A process for producing 5-iodo-2-methylbenzoic acid according to (8) or (9), wherein the separated and recovered microporous compound is calcined at 400 to 700° C.

(12) A process for producing 5-iodo-2-methylbenzoic acid according to (1), wherein the reaction step is performed in acetic acid serving as a solvent.

(13) A process for producing 5-iodo-2-methylbenzoic acid according to (1), wherein the purification step is crystallization in which a product is precipitated through cooling or addition of water.

(14) A process for producing 5-iodo-2-methylbenzoic acid according to (13), wherein the product is precipitated by adding 0.1 to 5 parts by weight of water to 1 part by weight of formed reaction mixture.

(15) A process for producing 5-iodo-2-methylbenzoic acid according to (13) or (14), wherein the formed reaction mixture is subjected to crystallization at 10 to 80° C. for purification.

(16) A process for producing 5-iodo-2-methylbenzoic acid according to (13), wherein, after crystallization, the solvent is removed from a mother liquor, and a portion of the residue obtained after removal of the solvent is recycled in a crystallization system.

(17) High-purity 5-iodo-2-methylbenzoic acid produced through any of processes (1) to (16), which has a 5-iodo-2-methylbenzoic acid purity of 99% or higher and which contains iodine, an iodine compound, an inorganic salt, a transition metal compound, a microporous compound, and a metal oxide in a total amount of 500 ppm or less as impurities.

BEST MODES FOR CARRYING OUT THE INVENTION

No particular limitation is imposed on the grade of 2-methylbenzoic acid serving as a starting material in the present invention, so long as the compound is available in the industry. However, the purity of the compound is preferably 98% or higher so as to enhance the purity of the final product.

Upon iodination, iodine and an oxidizing agent were employed in the presence of a microporous compound. Among oxidizing agents, iodic acid and/or periodic acid are particularly preferred. The iodination reaction proceeds through exclusive use of iodine. However, since a compound having an electron-attractive group such as 2-methylbenzoic acid has poor reactivity, the reactivity must be enhanced through use of an oxidizing agent in combination.

Iodine, iodic acid, and periodic acid are in the form of solid at ambient temperature. In use, these species may be used in the form of solid, or in the form of solution or suspension with an appropriate solvent.

During the reaction step, water is generated in the course of reaction. In this case, the thus-generated water is removed through addition of a dehydrating agent, whereby reaction is promoted, thereby attaining high conversion. The dehydrating agent preferably interacts exclusively with water and does not react with other components in the reaction system. Examples of the dehydrating agent include inorganic compounds such as sodium sulfate anhydrate, magnesium sulfate anhydrate, and calcium chloride; and carboxylic acid anhydrides such as acetic anhydride, propionic anhydride, pyvalic anhydride, and phthalic anhydride. Among them, acetic anhydride is employed in the present invention, from the viewpoint of ease of separation and purification after reaction.

The microporous compound, which is employed in the reaction, is a compound having micropores of some nanometers, and examples include zeolite. Specific examples of the zeolite include 8-membered-ring-form zeolites such as ABW, AEI, AFX, APC, ATN, ATT, ATV, AWW, CHA, DDR, EAB, ERI, GIS, JBW, KFI, LEV, LTA, MER, MON, PAU, PHI, RHO, RTE, RTH, and VNI; 9-membered-ring-form zeolites such as CHI, LOV, RSN, and VSV; 10-membered-ring-form zeolites such as DAC, EPI, FER, LAU, MEL, MFI, MFS, MTT, NES, TON, and WEI; and 12-membered-ring-form zeolites such as AFS, AFY, ATO, CAN, GME, MAZ, MEI, MTW, OFF, RON, and VET. Note that these three letter codes are zeolite structure identifying codes as stipulated by IUPAC. More specific examples include chabazite, zeolites A, X, Y, L, and ZSM-5, mordenite, and β-form zeolite. In the reaction of the present invention, a zeolite species having a micropore size of 0.5 nm or more is preferred, with β-form zeolite being particularly preferably employed.

The β-form zeolite preferably has a mole ratio of Si to Al, these elements forming the skeleton thereof, of 10 to 250. In preferably employed zeolite species, other than Si, Al, and O, which generally form a zeolite skeleton, any of the elements such as Na, K, Cs, Ca, Mg, Ti, Sn, Fe, Ni, Zn, Pd, and Ag is present within or outside the skeleton, which is incorporated into zeolite naturally or through an artificial means such as hydrothermal synthesis, ion exchange, or ion impregnation.

The microporous compound employed in the invention may be powder of crystals, a compacted/pulverized product, an extruded product, or pellets.

No particular limitation is imposed on the mode of iodination reaction, and iodination of 2-methylbenzoic acid may be carried out in a batch manner, a semi-batch manner, a complete mixed flow manner, a flow-on-immobilized bed manner, etc. The mode of reaction may be selected in accordance with the production scale. In the case of small-scale production, a batch manner is appropriate, whereas in the case of mass production, continuous modes such as a complete mixed flow manner and a flow-on-immobilized bed manner are more effective production methods.

The reaction temperature is 50 to 200° C., preferably 70 to 150° C. Through controlling the reaction temperature so as to fall within the ranges, sufficient rate of reaction can be attained while side reaction such as formation of high-boiling-point substances is prevented. The reaction pressure (absolute pressure) is 0.005 to 2 MPa, preferably 0.01 to 1 MPa.

Since 2-methylbenzoic acid has a melting point of 105° C., iodination thereof is performed at a temperature equal to or higher than the melting point, reaction solvent is not necessarily employed. Generally, an organic solvent that is inert with respect to iodination is preferably employed, and examples of the organic solvent include acetic acid, trifluoroacetic acid, dichloromethane, tetrachlorocarbon, dichlorobenzene, and chlorobenzene. Among them, acetic acid is particularly preferably employed. The solvent is preferably employed in an amount of 0.5 to 100 parts by weight on the basis of 1 part by weight of 2-methylbenzoic acid, more preferably 1 to 50 parts by weight.

No particular limitation is imposed on the amount of iodine, and iodine is appropriately used in an amount of 0.1 to 1.5 parts by weight on the basis of 1 part by weight of 2-methylbenzoic acid, preferably 0.5 to 1 part by weight, in order to enhance conversion of 2-methylbenzoic acid. The oxidizing agent such as iodic acid or periodic acid is preferably used in an amount of 0.01 to 1 part by weight on the basis of 1 part by weight of iodine, more preferably 0.05 to 0.5 parts by weight.

The microporous compound is used in an amount of 0.05 parts by weight or more on the basis of 1 part by weight of 2-methylbenzoic acid serving as a starting material, preferably 0.1 parts by weight or more. When the amount of microporous compound is less than 0.05 parts by weight, sufficient reactivity is not attained. In this case, 5-iodo-2-methylbenzoic acid cannot be produced at high selectivity.

In use, the microporous compound is suspended in the reaction mixture. After completion of reaction, the microporous compound can readily be separated from the resultant mixture through a routine method such as sedimentation, centrifugation, or filtration. The thus-separated microporous compound can be recycled in the reaction system.

The thus-recovered microporous compound may be reused in reaction without any further treatment. Alternatively, the microporous compound may be reused in reaction after washing with an appropriate solvent so as to remove the reaction mixture liquid. Although no particular limitation is imposed on the solvent with which the microporous compound is washed, acetic acid, which also serves as a reaction solvent, is preferably employed from the viewpoint of simplicity of the process. The solvent for washing is preferably used in an amount of 1 to 10 parts by weight on the basis of 1 part by weight of the recovered microporous compound.

After the microporous compound has been repeatedly used in reaction, activity of the compound is known to be reduced due to adsorption of high-boiling-point substances or by other factors. The thus-reduced reactivity can be enhanced again through the below-described calcining treatment. The microporous compound recovered from the formed reaction mixture may be calcined without any further treatment. However, preferably, the microporous compound is washed with a solvent such as acetic acid, followed by calcining. After washing, the microporous compound is sufficiently dried at 100 to 150° C. preferably for two hours or longer. The thus-dried microporous compound is calcined in air preferably at 400 to 700° C. for 0.5 to 10 hours.

Acetic anhydride serving as a dehydrating agent is used in an amount of 0.01 to 2 parts by weight on the basis of 1 part by weight of 2-methylbenzoic acid serving as a starting material, preferably 0.1 to 1.5 parts by weight. Through controlling the amount of acetic anhydride so as to fall within the above ranges, a sufficient reaction-promoting effect can be attained, whereby conversion of 2-methylbenzoic acid serving as a starting material and that of iodine can be enhanced. Thus, 5-iodo-2-methylbenzoic acid can be produced at low cost without increasing load of separation/recovery during the purification step. Notably, in the case in which iodine, iodic acid, periodic acid, or a similar species is dissolved or suspended in water, and the solution or suspension is placed in a reactor, acetic anhydride must be added in an amount in excess of the above amount in order to remove water forming the solution or suspension.

As described above, in the present invention, reaction is carried out in a batch manner, a semi-batch manner, a complete mixed flow manner, etc. The time for reaction in a batch manner or a semi-batch manner, or the residence time for reaction in a complete mixed flow manner is generally 1 to 20 hours. In the case of a flow-on-immobilized bed manner, LHSV (liquid hourly space velocity) of 2-methylbenzoic acid is 0.05 to 1 h$^{-1}$.

The industrial process of the present invention for producing 5-iodo-2-methylbenzoic acid includes, as essential steps, an iodination reaction step and a purification step including sublimation, distillation, crystallization, or a combination of two or more of these. After iodination through the aforementioned manner, the crude product is subjected to sublimation, distillation, crystallization, or a similar treatment, whereby a high-purity product of 5-iodo-2-methylbenzoic acid can readily be isolated.

In the purification step, in order to form 5-iodo-2-methylbenzoic acid in a more simple and efficient manner, the product is preferably precipitated as crystals through cooling or addition of water (i.e., crystallization). Specifically, in the course of cooling of the reaction mixture, crystals start to precipitate at 90° C. or lower, and 70% or more of the formed 5-iodo-2-methylbenzoic acid are crystallized when cooled to 50° C. or lower. The thus-precipitated crystals may be collected through a means such as filtration. Alternatively, the crystals are obtained through addition of water. Specifically, when water in an amount of 0.1 to 5 parts by weight is added to 1 part by weight of the reaction mixture, 90% or more of the formed 5-iodo-2-methylbenzoic acid are precipitated. Generally, the thus-precipitated crystals are collected through filtration. In some cases, iodine is crystallized simultaneously with 5-iodo-2-methylbenzoic acid during addition of water. Such precipitation of iodine can be prevented by adding sodium sulfite, sodium hydrogensulfite, or sodium thiosulfate to the reaction mixture in advance. Sodium sulfite, sodium hydrogensulfite, or sodium thiosulfate may be added 0.05 parts by weight or less on the basis of 1 part by weight of iodine employed in the reaction, and such an amount is sufficient in the present invention.

In other words, through subjecting the reaction mixture to crystallization at 10 to 80° C., crystals of 5-iodo-2-methylbenzoic acid can be precipitated. In order to enhance percent recovery of the product, crystallization is more preferably performed at 10 to 50° C. Upon addition of water, water is added to the mixture in an amount of 0.1 to 5 parts by weight on the basis of 1 part by weight of the reaction mixture, preferably 0.3 to 2 parts by weight. The thus-precipitated crystals can be readily collected through filtration.

The acetic acid solvent which has been employed in the reaction step can readily be recovered through distillation of the mother liquor after collection of the precipitated crystals, and the recovered solvent may be reused in another cycle of the reaction step. In the distillation bottom product, 5-iodo-2-methylbenzoic acid which has been dissolved in the mother liquor is concentrated. Thus, through recycling the bottom product in the crystallization system, 5-iodo-2-methylbenzoic acid can also be recovered. The distillation bottom product also contains, in addition to the product, high-boiling-point substances at a high concentration. Thus, it is essential that a portion of the bottom product is not recycled in the crystallization system but removed from the distillation column. In order to enhance percent recovery of 5-iodo-2-methylbenzoic acid and prevent impairment in product purity, 50 to 90% of the component which has been formed through removal of the solvent from the mother liquor is recycled, which is appropriate.

According to the present invention, 5-iodo-2-methylbenzoic acid, which produced through a process for producing 5-iodo-2-methylbenzoic acid including, as essential steps, a reaction step of iodinating 2-methylbenzoic acid in the presence of a microporous compound, iodine, an oxidizing agent, and acetic anhydride, and a purification step including sublimation, distillation, crystallization, or a combination thereof, has a 5-iodo-2-methylbenzoic acid purity of 99% or higher and contains iodine, an iodine compound, an inorganic salt, a transition metal compound, zeolite, and a metal oxide in a total amount of 500 ppm or less as impurities, which is remarkably high purity.

The present invention will next be described in more detail by way of examples, which should not be construed as limiting the invention thereto. Hereinafter, unless otherwise specified, purity and other similar properties are on the basis of wt. %.

EXAMPLE 1

In a 200-mL three-neck flask equipped with a reflux condenser, acetic acid (76.5 g), acetic anhydride (23.5 g), 2-methylbenzoic acid (20.0 g), iodine (14.4 g), a 70% aqueous iodic acid solution (8.6 g), and H-β-form zeolite (4.6 g) were placed. The mixture was allowed to react at a reflux temperature of 122° C. for four hours. After completion of reaction, H-β-form zeolite was removed from the reaction mixture through filtration, and the filtrate was cooled to room temperature. The precipitated crystals were collected through filtration, to thereby yield 29.3 g (after drying) of a product. Through HPLC (high-performance liquid chromatography) analysis of the collected crystals and the mother liquor, the following reaction results were obtained.

| | |
|---|---|
| 2-methylbenzoic acid: | 97.0% (conversion) |
| 5-iodo-2-methylbenzoic acid: | 92.0% (yield) |
| | 94.8% (selectivity) |
| 3-iodo-2-methylbenzoic acid: | 0.7% (yield) |
| | 0.7% (selectivity) |
| 5-iodo-2-methylbenzoic acid crystals: | 75.9% (yield) |
| 5-iodo-2-methylbenzoic acid: | 99.7% (purity in crystals) |

The thus-obtained crystals (1 g) were dissolved in methanol (25 mL), and a 4% aqueous KI solution (25 mL) and 17% sulfuric acid (5 mL) were added to the solution. The resultant solution was titrated with a 0.02M aqueous sodium thiosulfate solution. The free iodine content was found to be 5 ppm. Through ICP-basis total element analysis, Li, Na, K, Mg, Ca, Sr, Ba, Sc, Y, Ti, Zr, V, Nb, Cr, Mo, W, Mn, Fe, Ru, Co, Rh, Ni, Pd, Pt, Cu, Ag, Au, Zn, Cd, Al, In, Si, Sn, Pb, P, Sb, or S was not detected, and the Group 1 element content and the Group 2 element content were both 1 ppm or less.

EXAMPLE 2

The procedure of Example 1 was repeated, except that acetic acid (96.0 g), acetic anhydride (9.2 g), iodine (15.6 g), and periodic acid (5.5 g) instead of iodic acid were employed, to thereby yield 28.5 g of a product. The following reaction analysis results were obtained.

| | |
|---|---|
| 2-methylbenzoic acid: | 93.0% (conversion) |
| 5-iodo-2-methylbenzoic acid: | 89.3% (yield) |
| | 96.0% (selectivity) |
| 3-iodo-2-methylbenzoic acid: | 0.2% (yield) |
| | 0.2% (selectivity) |
| 5-iodo-2-methylbenzoic acid crystals: | 73.7% (yield) |
| 5-iodo-2-methylbenzoic acid: | 99.5% (purity in crystals) |

Through analysis of the thus-obtained crystals, the free iodine content was found to be 5 ppm, and Li, Na, K, Mg, Ca, Sr, Ba, Sc, Y, Ti, Zr, V, Nb, Cr, Mo, W, Mn, Fe, Ru, Co, Rh, Ni, Pd, Pt, Cu, Ag, Au, Zn, Cd, Al, In, Si, Sn, Pb, P, Sb, or S was not detected. The Group 1 element content and the Group 2 element content were both 1 ppm or less.

EXAMPLE 3

The reaction of Example 1 was repeated under the same conditions, and H-β-form zeolite was removed from the reaction mixture through filtration. Water (50.0 g) was added to the filtrate, followed by cooling to room temperature. The precipitated crystals were collected through filtration, to thereby yield 33.0 g of a product. The following reaction analysis results were obtained.

| | |
|---|---|
| 2-methylbenzoic acid: | 97.0% (conversion) |
| 5-iodo-2-methylbenzoic acid: | 92.0% (yield) |
| | 94.8% (selectivity) |
| 3-iodo-2-methylbenzoic acid: | 0.7% (yield) |
| | 0.7% (selectivity) |
| 5-iodo-2-methylbenzoic acid crystals: | 85.6% (yield) |
| 5-iodo-2-methylbenzoic acid: | 99.8% (purity in crystals) |

Through analysis of the thus-obtained crystals, the free iodine content was found to be 5 ppm, and Li, Na, K, Mg, Ca, Sr, Ba, Sc, Y, Ti, Zr, V, Nb, Cr, Mo, W, Mn, Fe, Ru, Co, Rh, Ni, Pd, Pt, Cu, Ag, Au, Zn, Cd, Al, In, Si, Sn, Pb, P, Sb, or S was not detected. The Group 1 element content and the Group 2 element content were both 1 ppm or less.

EXAMPLE 4

The filtrate of Example 1 after collection of crystals was concentrated, to thereby obtain 9.1 g of crystals. A portion of the crystals (80%, 7.3 g) was recycled in the crystallization system. The crystals to be recycled were dissolved in the liquid which had been formed through the same reaction as performed in Example 1 and from which H-β-form zeolite had been removed. The solution was subjected to crystallization, and the thus-precipitated crystals were collected through filtration, to thereby yield 34.3 g of a product. The purity of the crystals in terms of 5-iodo-2-methylbenzoic acid was found to be 99.6%. Through analysis of the thus-obtained crystals, the free iodine content was found to be 5 ppm, and Li, Na, K, Mg, Ca, Sr, Ba, Sc, Y, Ti, Zr, V, Nb, Cr, Mo, W, Mn, Fe, Ru, Co, Rh, Ni, Pd, Pt, Cu, Ag, Au, Zn, Cd, Al, In, Si, Sn, Pb, P, Sb, or S was not detected. The Group 1 element content and the Group 2 element content were both 1 ppm or less. In Example 1, 29.3 g of crystals of 5-iodo-2-methylbenzoic acid were obtained. The results of Example 4 indicated that percent recovery of 5-iodo-2-methylbenzoic acid can be enhanced without impairing product purity through recycling a component contained in the mother liquor after crystallization.

COMPARATIVE EXAMPLE 1

To a 100-mL three-neck flask equipped with a reflux condenser, 30% sulfuric acid (25 mL) and 2-methylbenzoic acid (1.36 g, 10 mmol) were fed to form a suspension. Iodine monochloride (2.4 g, 15 mmol) was added dropwise to the suspension. The mixture was allowed to react at 90° C. for five hours, and the reaction mixture was poured into water (90 mL). The precipitated product was collected through filtration, followed by washing with an aqueous sodium sulfite solution, to thereby yield a crystalline solid as a reaction product (yield: 1.6 g). The following reaction analysis results were obtained.

| | |
|---|---|
| 2-methylbenzoic acid: | 52.0% (conversion) |
| 5-iodo-2-methylbenzoic acid: | 40.6% (yield) |
| | 78.0% (selectivity) |
| 3-iodo-2-methylbenzoic acid: | 12.0% (yield) |
| | 23.0% (selectivity) |
| 5-iodo-2-methylbenzoic acid crystals: | 23.2% (yield) |
| 5-iodo-2-methylbenzoic acid: | 38.0% (purity in crystals) |

The above mixture was purified through recrystallization from acetic acid, isopropyl alcohol, or a similar solvent, so as to isolate 5-iodo-2-methylbenzoic acid. However, the purity of the mixture was not virtually enhanced, and 5-iodo-2-methylbenzoic acid was difficult to obtain.

COMPARATIVE EXAMPLE 2

In the same apparatus as employed in Example 1, acetic acid (92 mL), 2-methylbenzoic acid (15.0 g), iodine (12.0 g), a 50% aqueous periodic acid solution (7.2 g), and concentrated sulfuric acid (4.7 g) were placed. The mixture was allowed to react at a reflux temperature of 120° C. for seven hours. After completion of reaction, the reaction mixture was cooled to room temperature. The precipitated crystals were collected through filtration, to thereby yield 16.4 g of a product. The following reaction analysis results were obtained.

| | |
|---|---|
| 2-methylbenzoic acid: | 94.0% (conversion) |
| 5-iodo-2-methylbenzoic acid: | 69.0% (yield) |
| | 73.4% (selectivity) |
| 3-iodo-2-methylbenzoic acid: | 20.0% (yield) |
| | 21.3% (selectivity) |
| 5-iodo-2-methylbenzoic acid crystals: | 54.0% (yield) |
| 5-iodo-2-methylbenzoic acid: | 95.0% (purity in crystals) |

Thus, when concentrated sulfuric acid was employed as an acid catalyst, purity and yield of 5-iodo-2-methylbenzoic acid were unsatisfactory.

COMPARATIVE EXAMPLE 3

The procedure of Example 1 was repeated, except that iodic acid was not employed, to thereby yield 5 g of a product. The following reaction analysis results were obtained.

| | |
|---|---|
| 2-methylbenzoic acid: | 15.8% (conversion) |
| 5-iodo-2-methylbenzoic acid: | 9.5% (yield) |
| | 60.1% (selectivity) |
| 3-iodo-2-methylbenzoic acid: | 2.8% (yield) |
| | 18.0% (selectivity) |
| 5-iodo-2-methylbenzoic acid crystals: | 7.4% (yield) |
| 5-iodo-2-methylbenzoic acid: | 57.0% (purity in crystals) |

Thus, when iodic acid was not employed, purity and yield of 5-iodo-2-methylbenzoic acid were unsatisfactory.

COMPARATIVE EXAMPLE 4

The procedure of Example 1 was repeated, except that acetic anhydride was not employed, to thereby yield 18.5 g of a product. The following reaction analysis results were obtained.

| | |
|---|---|
| 2-methylbenzoic acid: | 65.8% (conversion) |
| 5-iodo-2-methylbenzoic acid: | 60.2% (yield) |
| | 91.5% (selectivity) |
| 3-iodo-2-methylbenzoic acid: | 2.2% (yield) |
| | 3.3% (selectivity) |
| 5-iodo-2-methylbenzoic acid crystals: | 45.8% (yield) |
| 5-iodo-2-methylbenzoic acid: | 95.2% (purity in crystals) |

Thus, when acetic anhydride was not employed, purity and yield of 5-iodo-2-methylbenzoic acid were unsatisfactory.

EXAMPLE 5

In a 10-L reactor equipped with a reflux condenser, acetic acid (2,678 g), acetic anhydride (823 g), 2-methylbenzoic acid (700 g), iodine (502 g), a 70% aqueous iodic acid solution (299 g), and H-β-form zeolite (161 g) were placed. The mixture was allowed to react at a reflux temperature of 122° C. for four hours. After completion of reaction, H-β-form zeolite was removed from the reaction mixture through filtration through suction by use of a membrane filter. The H-β-form zeolite left on the filter was washed with acetic acid (350 g), and the wash liquid and the filtrate were combined, followed by cooling to room temperature. The precipitated crystals were collected through filtration, to thereby yield 970 g (after drying) of a product. Through HPLC (high-performance liquid chromatography) analysis of the collected crystals and the mother liquor, the following reaction results were obtained.

| | |
|---|---|
| 2-methylbenzoic acid: | 97.0% (conversion) |
| 5-iodo-2-methylbenzoic acid: | 94.3% (yield) |
| | 97.2% (selectivity) |
| 3-iodo-2-methylbenzoic acid: | 0.7% (yield) |
| | 0.7% (selectivity) |
| 5-iodo-2-methylbenzoic acid: | 99.7% (purity in crystals) |

EXAMPLE 6

In Example 6, H-β-form zeolite (245 g) which had been recovered after filtration and washing performed in Example 5 was used. In a manner similar to that of Example 5, reaction, separation/recovery of H-β-form zeolite, and recovery of reaction products from mother liquor were repeatedly carried out. The results are shown in Table 1. As is clear from Table 1, excellent results were obtained in repetition of operations. However, after completion of the sixth reaction, conversion of 2-methylbenzoic acid and yield of 5-iodo-2-methylbenzoic acid were lowered.

TABLE 1

| Reaction | 1st | 2nd | 3rd | 4th | 5th | 6th |
|---|---|---|---|---|---|---|
| Conversion[1] | 97.0 | 97.5 | 97.2 | 96.7 | 95.9 | 93.0 |
| Yield[2] | 94.3 | 94.5 | 94.5 | 93.8 | 92.9 | 90.2 |
| Selectivity[3] | 97.2 | 96.9 | 97.2 | 97.0 | 96.9 | 97.0 |
| Crystal purity[4] | 99.7 | 99.7 | 99.7 | 99.7 | 99.6 | 99.6 |

[1]2-methylbenzoic acid (conversion) (%)
[2]5-iodo-2-methylbenzoic acid (yield) (%)
[3]5-iodo-2-methylbenzoic acid (selectivity) (%)
[4]5-iodo-2-methylbenzoic acid (purity in crystals) (%)

The same definitions are applied to the following Tables.

EXAMPLE 7

The procedure of Example 5 was repeated, except that H-β-form zeolite separated through filtration from the reaction mixture was recovered without washing with acetic acid. The following reaction analysis results were obtained.

| | |
|---|---|
| 2-methylbenzoic acid: | 97.0% (conversion) |
| 5-iodo-2-methylbenzoic acid: | 94.1% (yield) |
| | 97.0% (selectivity) |
| 3-iodo-2-methylbenzoic acid: | 0.7% (yield) |
| | 0.7% (selectivity) |
| 5-iodo-2-methylbenzoic acid: | 99.7% (purity in crystals) |

EXAMPLE 8

In Example 8, H-β-form zeolite (287 g) which had been separated from the reaction mixture in Example 7 but had not been washed with acetic acid was used. In a manner similar to that of Example 7, reaction, separation/recovery of H-β-form zeolite, and recovery of reaction products from mother liquor were repeatedly carried out. The results are shown in Table 2. As is clear from Table 2, excellent results were obtained in repetition of operations. However, after completion of the sixth reaction, conversion of 2-methylbenzoic acid and yield of 5-iodo-2-methylbenzoic acid were lowered.

TABLE 2

| Reaction | 1st | 2nd | 3rd | 4th | 5th | 6th |
|---|---|---|---|---|---|---|
| Conversion[1] | 97.0 | 97.2 | 97.2 | 96.8 | 96.0 | 94.2 |
| Yield[2] | 94.1 | 94.6 | 94.6 | 93.7 | 93.2 | 89.8 |
| Selectivity[3] | 97.0 | 97.3 | 97.3 | 96.8 | 97.1 | 95.8 |
| Crystal purity[4] | 99.7 | 99.7 | 99.7 | 99.7 | 99.6 | 99.6 |

EXAMPLE 9

The reaction was repeatedly performed six times in a manner similar to that of Example 6 including washing zeolite with acetic acid. After completion of reactions, H-β-form zeolite (238 g) was recovered. The thus-recovered H-β-form zeolite was placed in a muffle furnace, where zeolite was dried at 150° C. for two hours in air and then calcined at 550° C. for three hours. The calcined H-β-form zeolite had a weight of 150 g. In a manner similar to that of Example 5 or 6, reaction operations were repeated utilizing the obtained H-β-form zeolite. As is clear from Table 3 below, excellent reaction results were obtained again after the seventh reaction.

TABLE 3

| | Reaction | | | |
|---|---|---|---|---|
| | 7th | 8th | 9th | 10th |
| Conversion[1] | 97.0 | 97.5 | 97.2 | 96.7 |
| Yield[2] | 94.3 | 94.7 | 94.4 | 93.8 |
| Selectivity[3] | 97.2 | 97.1 | 97.1 | 97.0 |
| Crystal purity[4] | 99.7 | 99.7 | 99.7 | 99.7 |

EXAMPLE 10

The reaction was repeatedly performed six times in a manner similar to that of Example 6. Subsequently, the reaction was further repeated in the same manner. The reaction results are shown in Table 4.

TABLE 4

| Reaction | 7th | 8th | 9th | 10th |
|---|---|---|---|---|
| Conversion[1] | 88.2 | 80.2 | 68.5 | 50.2 |
| Yield[2] | 84.2 | 76.8 | 64.7 | 46.3 |
| Selectivity[3] | 95.5 | 95.8 | 94.5 | 92.2 |
| Crystal purity[4] | 99.6 | 99.5 | 99.5 | 99.1 |

EXAMPLE 11

The procedure of Example 9 was repeated, except that the calcining temperature was adjusted to 380° C. As is clear from Table 5 below, catalytic activity was revived to a certain extent. However, as is clear from the Table 5, the activity was lowered as the reaction repeated.

TABLE 5

| Reaction | 7th | 8th | 9th | 10th |
|---|---|---|---|---|
| Conversion[1] | 95.2 | 90.2 | 82.5 | 70.2 |
| Yield[2] | 90.4 | 87.0 | 78.2 | 66.2 |
| Selectivity[3] | 95.0 | 96.5 | 94.8 | 94.3 |
| Crystal purity[4] | 99.7 | 99.6 | 99.5 | 99.5 |

EXAMPLE 12

In a 10-L reactor equipped with a reflux condenser, acetic acid (2,678 g), acetic anhydride (823 g), 2-methylbenzoic acid (700 g), iodine (502 g), a 70% aqueous iodic acid solution (299 g), and H-β-form zeolite (161 g) were placed. The mixture was allowed to react at a reflux temperature of 122° C. for four hours. After completion of reaction, H-β-form zeolite was removed from the reaction mixture through filtration, and the filtrate was cooled to 30° C. The precipitated white crystals were collected through filtration, to thereby yield 1,042 g (after drying) of a product. Through HPLC (high-performance liquid chromatography) analysis of the collected crystals and the mother liquor, the following reaction results were obtained.

| | |
|---|---|
| 2-methylbenzoic acid: | 97.0% (conversion) |
| 5-iodo-2-methylbenzoic acid: | 94.3% (yield) |
| | 97.2% (selectivity) |
| 3-iodo-2-methylbenzoic acid: | 0.7% (yield) |
| | 0.7% (selectivity) |
| 5-iodo-2-methylbenzoic acid crystals: | 77.3% (yield) |
| 5-iodo-2-methylbenzoic acid: | 99.7% (purity in crystals) |

The thus-obtained crystals (1 g) were dissolved in methanol (25 mL), and a 4% aqueous KI solution (25 mL) and 17% sulfuric acid (5 mL) were added to the solution. The resultant solution was titrated with a 0.02M aqueous sodium thiosulfate solution. The iodine content was found to be 5 ppm. Through ICP-basis total element analysis, Li, Na, K, Mg, Ca, Sr, Ba, Sc, Y, Ti, Zr, V, Nb, Cr, Mo, W, Mn, Fe, Ru, Co, Rh, Ni, Pd, Pt, Cu, Ag, Au, Zn, Cd, Al, In, Si, Sn, Pb, P, Sb, or S was not detected, and the Group 1 element content and the Group 2 element content were both 1 ppm or less.

EXAMPLE 13

The procedure of Example 12 was repeated, except that acetic acid (3,360 g), acetic anhydride (322 g), iodine (544 g), and periodic acid (191 g) instead of iodic acid were employed, to thereby yield 994 g of a product as white crystals. The following reaction analysis results were obtained.

| | |
|---|---|
| 2-methylbenzoic acid: | 93.0% (conversion) |
| 5-iodo-2-methylbenzoic acid: | 90.0% (yield) |
| | 96.8% (selectivity) |
| 3-iodo-2-methylbenzoic acid: | 0.2% (yield) |
| | 0.2% (selectivity) |
| 5-iodo-2-methylbenzoic acid crystals: | 73.7% (yield) |
| 5-iodo-2-methylbenzoic acid: | 99.5% (purity in crystals) |

Through analysis of the thus-obtained crystals, the iodine content was found to be 5 ppm, and Li, Na, K, Mg, Ca, Sr, Ba, Sc, Y, Ti, Zr, V, Nb, Cr, Mo, W, Mn, Fe, Ru, Co, Rh, Ni, Pd, Pt, Cu, Ag, Au, Zn, Cd, Al, In, Si, Sn, Pb, P, Sb, or S was not detected. The Group 1 element content and the Group 2 element content were both 1 ppm or less.

EXAMPLE 14

The filtrate of Example 12 after collection of crystals was concentrated, to thereby obtain 302 g of crystals. A portion of the crystals (80%, 242 g) was recycled in the crystallization system. The crystals to be recycled were dissolved in the liquid which had been formed through the same reaction as performed in Example 12 and from which H-β-form zeolite had been removed. The solution was subjected to crystallization, and the thus-precipitated white crystals were collected through filtration, to thereby yield 1,210 g of a product. The purity of the crystals in terms of 5-iodo-2-methylbenzoic acid was found to be 99.6%. Through analysis of the thus-obtained crystals, the iodine content was found to be 5 ppm, and Li, Na, K, Mg, Ca, Sr, Ba, Sc, Y, Ti, Zr, V, Nb, Cr, Mo, W, Mn, Fe, Ru, Co, Rh, Ni, Pd, Pt, Cu, Ag, Au, Zn, Cd, Al, In, Si, Sn, Pb, P, Sb, or S was not detected. The Group 1 element content and the Group 2 element content were both 1 ppm or less. In Example 12, 1,042 g of crystals of 5-iodo-2-methylbenzoic acid were obtained. The results of Example 14 indicated that percent recovery of 5-iodo-2-methylbenzoic acid can be enhanced without impairing product purity through recycling a component contained in the mother liquor after crystallization.

COMPARATIVE EXAMPLE 5

In the same apparatus as employed in Example 12, acetic acid (3,680 mL), 2-methylbenzoic acid (600 g), iodine (480 g), a 50% aqueous periodic acid solution (288 g), and concentrated sulfuric acid (188 g) were placed. The mixture was allowed to react at a reflux temperature of 120° C. for seven hours. After completion of reaction, the reaction mixture was cooled to 30° C. The precipitated pale gray crystals were collected through filtration, to thereby yield 624 g of a product. The following reaction analysis results were obtained.

| | |
|---|---|
| 2-methylbenzoic acid: | 94.0% (conversion) |
| 5-iodo-2-methylbenzoic acid: | 69.0% (yield) |
| | 73.4% (selectivity) |
| 3-iodo-2-methylbenzoic acid: | 20.0% (yield) |
| | 21.3% (selectivity) |
| 5-iodo-2-methylbenzoic acid crystals: | 54.0% (yield) |
| 5-iodo-2-methylbenzoic acid: | 95.0% (purity in crystals) |

Through analysis of the thus-obtained crystals, the iodine content was found to be 620 ppm. Through ICP-basis total element analysis, Li, Na, K, Mg, Ca, Sr, Ba, Sc, Y, Ti, Zr, V, Nb, Cr, Mo, W, Mn, Fe, Ru, Co, Rh, Ni, Pd, Pt, Cu, Ag, Au, Zn, Cd, Al, In, Si, Sn, Pb, P, Sb, or S was not detected. The Group 1 element content and the Group 2 element content were both 1 ppm or less.

Thus, when concentrated sulfuric acid was employed as an acid catalyst, purity and yield of 5-iodo-2-methylbenzoic acid were unsatisfactory.

COMPARATIVE EXAMPLE 6

Crystals (100 g) of 5-iodo-2-methylbenzoic acid (purity: 95.0%) which had been produced in Comparative Example 5 were dissolved in acetic acid (2,000 g) at 90° C., and the solution was cooled to 30° C. The precipitated pale gray crystals (60 g) were collected through filtration. Through HPLC analysis, the crystals were found to have a purity in terms of 5-iodo-2-methylbenzoic acid of 98%. Through analysis of the thus-obtained crystals, the iodine content was found to be 545 ppm. Through ICP-basis total element analysis, Li, Na, K, Mg, Ca, Sr, Ba, Sc, Y, Ti, Zr, V, Nb, Cr, Mo, W, Mn, Fe, Ru, Co, Rh, Ni, Pd, Pt, Cu, Ag, Au, Zn, Cd, Al, In, Si, Sn, Pb, P, Sb, or S was not detected. The Group 1 element content and the Group. 2 element content were both 1 ppm or less.

Thus, when concentrated sulfuric acid was employed as an acid catalyst, the formed 5-iodo-2-methylbenzoic acid crystals had a high iodine content, although recrystallization was performed. The results also indicated that high-purity 5-iodo-2-methylbenzoic acid was not produced in Comparative Example 6.

COMPARATIVE EXAMPLE 7

The procedure of Example 12 was repeated, except that acetic anhydride was not employed, to thereby yield 598 g of a product. The following reaction analysis results were obtained.

| | |
|---|---|
| 2-methylbenzoic acid: | 65.8% (conversion) |
| 5-iodo-2-methylbenzoic acid: | 60.2% (yield) |
| | 91.5% (selectivity) |
| 3-iodo-2-methylbenzoic acid: | 2.2% (yield) |
| | 3.3% (selectivity) |
| 5-iodo-2-methylbenzoic acid crystals: | 45.8% (yield) |
| 5-iodo-2-methylbenzoic acid: | 95.2% (purity in crystals) |

Through analysis of the thus-obtained crystals, the iodine content was found to be 480 ppm. Through ICP-basis total element analysis, Li, Na, K, Mg, Ca, Sr, Ba, Sc, Y, Ti, Zr, V, Nb, Cr, Mo, W, Mn, Fe, Ru, Co, Rh, Ni, Pd, Pt, Cu, Ag, Au, Zn, Cd, Al, In, Si, Sn, Pb, P, Sb, or S was not detected. The Group 1 element content and the Group 2 element content were both 1 ppm or less.

Thus, when acetic anhydride was not employed, purity and yield of 5-iodo-2-methylbenzoic acid were unsatisfactory.

EXAMPLE 15

In a 10-L reactor equipped with a reflux condenser, acetic acid (2,678 g), acetic anhydride (823 g), 2-methylbenzoic acid (700 g), iodine (502 g), a 70% aqueous iodic acid solution (299 g), and H-β-form zeolite (161 g) were placed. The mixture was allowed to react at a reflux temperature of 122° C. for four hours. After completion of reaction, H-β-form zeolite was removed from the reaction mixture through filtration. A 10% aqueous sodium thiosulfate solution (200 g) and water (2,500 g) were added to the filtrate, and the mixture was cooled to 30° C. The precipitated crystals were collected through filtration, to thereby yield 1,204 g (after drying) of a product. Through HPLC (high-performance liquid chromatography) analysis of the collected crystals and the mother liquor, the following reaction results were obtained.

| | |
|---|---|
| 2-methylbenzoic acid: | 97.0% (conversion) |
| 5-iodo-2-methylbenzoic acid: | 94.3% (yield) |
| | 97.2% (selectivity) |
| 3-iodo-2-methylbenzoic acid: | 0.7% (yield) |
| | 0.7% (selectivity) |
| 5-iodo-2-methylbenzoic acid crystals: | 89.6% (yield) |
| 5-iodo-2-methylbenzoic acid: | 99.7% (purity in crystals) |

The thus-obtained crystals (1 g) were dissolved in methanol (25 mL), and a 4% aqueous KI solution (25 mL) and 17% sulfuric acid (5 mL) were added to the solution. The resultant solution was titrated with a 0.02M aqueous sodium thiosulfate solution. The iodine content was found to be 5 ppm. Through ICP-basis total element analysis, Li, Na, K, Mg, Ca, Sr, Ba, Sc, Y, Ti, Zr, V, Nb, Cr, Mo, W, Mn, Fe, Ru, Co, Rh, Ni, Pd, Pt, Cu, Ag, Au, Zn, Cd, Al, In, Si, Sn, Pb, P, Sb, or S was not detected, and the Group 1 element content and the Group 2 element content were both 1 ppm or less.

EXAMPLE 16

The procedure of Example 15 was repeated, except that acetic acid (3,360 g), acetic anhydride (322 g), iodine (544 g), and periodic acid (191 g) instead of iodic acid were employed, to thereby yield 1.149 g of a product. The following reaction analysis results were obtained.

| | |
|---|---|
| 2-methylbenzoic acid: | 93.0% (conversion) |
| 5-iodo-2-methylbenzoic acid: | 90.0% (yield) |
| | 96.8% (selectivity) |
| 3-iodo-2-methylbenzoic acid: | 0.2% (yield) |
| | 0.2% (selectivity) |
| 5-iodo-2-methylbenzoic acid crystals: | 85.2% (yield) |
| 5-iodo-2-methylbenzoic acid: | 99.5% (purity in crystals) |

Through analysis of the thus-obtained crystals, the iodine content was found to be 5 ppm, and Li, Na, K, Mg, Ca, Sr, Ba, Sc, Y, Ti, Zr, V, Nb, Cr, Mo, W, Mn, Fe, Ru, Co, Rh, Ni, Pd, Pt, Cu, Ag, Au, Zn, Cd, Al, In, Si, Sn, Pb, P, Sb, or S was not detected. The Group 1 element content and the Group 2 element content were both 1 ppm or less.

EXAMPLE 17

The filtrate of Example 15 after collection of crystals was concentrated, to thereby obtain 140 g of crystals. A portion of the crystals (90%, 126 g) was recycled in the crystallization system. The crystals to be recycled were dissolved in the liquid which had been formed through the same reaction as performed in Example 15 and from which H-β-form zeolite had been removed. A 10% aqueous sodium thiosulfate solution (200 g) and water (2,500 g) were added to the solution, followed by cooling to 30° C. The precipitated crystals were collected through filtration, to thereby yield 1,228 g of a product. The purity of the crystals in terms of 5-iodo-2-methylbenzoic acid was found to be 99.6%. Through analysis of the thus-obtained crystals, the iodine content was found to be 5 ppm, and Li, Na, K, Mg, Ca, Sr, Ba, Sc, Y, Ti, Zr, V, Nb, Cr, Mo, W, Mn, Fe, Ru, Co, Rh, Ni, Pd, Pt, Cu, Ag, Au, Zn, Cd, Al, In, Si, Sn, Pb, P, Sb, or S was not detected. The Group 1 element content and the Group 2 element content were both 1 ppm or less. In Example 14, 1,204 g of crystals of 5-iodo-2-methylbenzoic acid were obtained. The results of Example 17 indicated that percent recovery of 5-iodo-2-methylbenzoic acid can be enhanced without impairing product purity through recycling a component contained in the mother liquor after crystallization.

INDUSTRIAL APPLICABILITY

According to the present invention, 5-iodo-2-methylbenzoic acid, which is useful for producing functional chemicals such as drugs, can be produced at high purity and high yield in a simple manner. Since the production process includes a simple reaction step and a simple separation/purification step, the load of purification is mitigated. In addition, the microporous compound such as a zeolite catalyst which has been separated and recovered from the reaction mixture can be repeatedly employed after performing of a simple treatment. Thus, the production process ensures a long service life of catalysts and high efficiency.

Therefore, the present invention is of remarkably great value, since the invention realizes production of 5-iodo-2-methylbenzoic acid on an industrial scale in an advantageous manner.

The invention claimed is:

1. A process for producing 5-iodo-2-methylbenzoic acid through iodination of 2-methylbenzoic acid, characterized in that the process comprises, as essential steps, a reaction step of iodinating 2-methylbenzoic acid in the presence of a H-β-form zeolite, wherein the H-β-form zeolite has an Si/Al mole ratio of 10 to 250, iodine, at least one of iodic acid and periodic acid, acetic anhydride and acetic acid, and a purification step including sublimation, distillation, crystallization, or a combination of two or more of these.

2. A process for producing 5-iodo-2-methylbenzoic acid as described in claim 1, wherein the H-β-form zeolite contains an element other than Si, Al, and O, which form a skeleton thereof, within or outside the skeleton.

3. A process for producing 5-iodo-2-methylbenzoic acid as described in claim 2, wherein the element other than Si, Al, and O, which form a skeleton of the H-β-form zeolite, is at least one member selected from among Na, K, Cs, Ca, Mg, Ti, Sn, Fe, Ni, Zn, Pb, and Ag.

4. A process for producing 5-iodo-2-methylbenzoic acid as described in claim 1, wherein the H-β-form zeolite is separated and recovered from a reaction mixture resulting from the reaction step, followed by re-employment in the reaction step.

5. A process for producing 5-iodo-2-methylbenzoic acid as described in claim 4, wherein the separated and recovered H-β-form zeolite is calcined, followed by re-employment in the reaction step.

6. A process for producing 5-iodo-2-methylbenzoic acid as described in claim 5, wherein the separated and recovered H-β-form zeolite is washed with a solvent, followed by calcining.

7. A process for producing 5-iodo-2-methylbenzoic acid as described in claim 6, wherein the separated and recovered H-β-form zeolite is washed with acetic acid serving as the solvent.

8. A process for producing 5-iodo-2-methylbenzoic acid as described in claim 5, wherein the separated and recovered H-β-form zeolite is calcined at 400 to 700° C.

9. A process for producing 5-iodo-2-methylbenzoic acid as described in claim 1, wherein the purification step is crystallization in which a product is precipitated through cooling or addition of water.

10. A process for producing 5-iodo-2-methylbenzoic acid as described in claim 9, wherein the product is precipitated by adding 0.1 to 5 parts by weight of water to 1 part by weight of formed reaction mixture.

11. A process for producing 5-iodo-2-methylbenzoic acid as described in claim 9, wherein the formed reaction mixture is subjected to crystallization at 10 to 80° C. for purification.

12. A process for producing 5-iodo-2-methylbenzoic acid as described in claim 9, wherein, after crystallization, the solvent is removed from a mother liquor, and a portion of the residue obtained after removal of the solvent is recycled in a crystallization system.

13. A process for producing 5-iodo-2-methylbenzoic acid as described in claim 6, wherein the separated and recovered H-β-form zeolite is calcined at 400 to 700° C.

14. A process for producing 5-iodo-2-methylbenzoic acid as described in claim 10, wherein the formed reaction mixture is subjected to crystallization at 10 to 80° C. for purification.

15. A process for producing 5-iodo-2-methylbenzoic acid as described in claim 1, wherein said acetic anhydride is employed as a dehydrating agent for water generated in the reaction step.

* * * * *